United States Patent
Webler, Jr. et al.

(10) Patent No.: US 9,358,369 B1
(45) Date of Patent: *Jun. 7, 2016

(54) REDUCED PROFILE AND ENHANCED FLEXIBILITY DELIVERY CATHETERS FOR LIGHT ACTIVATED AGENTS

(75) Inventors: William E. Webler, Jr., San Jose, CA (US); Richard R. Newhauser, Redwood City, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1164 days.

This patent is subject to a terminal disclaimer.

(21) Appl. No.: 12/190,862

(22) Filed: Aug. 13, 2008

(51) Int. Cl.
| | |
|---|---|
| *A61N 1/30* | (2006.01) |
| *A61M 25/06* | (2006.01) |
| *A61N 5/06* | (2006.01) |
| *A61B 1/00* | (2006.01) |

(52) U.S. Cl.
CPC ........ *A61M 25/0662* (2013.01); *A61B 1/00163* (2013.01); *A61B 1/00165* (2013.01); *A61N 5/062* (2013.01); *A61M 2025/0681* (2013.01)

(58) Field of Classification Search
CPC ............ A61B 1/00167; A61B 5/4839; A61M 2525/004
USPC ............ 604/20, 272; 600/478, 342, 463, 182; 606/115–116
See application file for complete search history.

(56) References Cited

U.S. PATENT DOCUMENTS

| | | | |
|---|---|---|---|
| 4,009,382 A | 2/1977 | Nath | |
| 4,566,438 A * | 1/1986 | Liese et al. | .................... 600/176 |
| 4,761,054 A | 8/1988 | Ishimori et al. | |
| 4,900,303 A | 2/1990 | Lemelson | |
| 5,042,494 A | 8/1991 | Alfano | |
| 5,201,730 A * | 4/1993 | Easley et al. | ...................... 606/4 |
| 5,412,750 A | 5/1995 | Nath | |
| 5,454,782 A | 10/1995 | Perkins | |
| 5,470,307 A * | 11/1995 | Lindall | .......................... 604/20 |
| 5,608,834 A | 3/1997 | Van Leeuwen | |
| 5,702,344 A | 12/1997 | Silverstein | |
| 5,709,653 A | 1/1998 | Leone | |
| 5,800,478 A | 9/1998 | Chen et al. | |
| 5,830,209 A | 11/1998 | Savage et al. | |
| 6,254,573 B1 | 7/2001 | Haim et al. | |
| 6,296,608 B1 * | 10/2001 | Daniels et al. | ................ 600/104 |
| 6,484,052 B1 | 11/2002 | Visuri et al. | |
| 6,749,623 B1 | 6/2004 | Hsi et al. | |
| 6,807,295 B1 | 10/2004 | Ono | |
| 6,811,562 B1 | 11/2004 | Pless | |
| 7,131,963 B1 | 11/2006 | Hyde | |

(Continued)

OTHER PUBLICATIONS

StockerYale Inc., "Custom-Engineered LED Solutions", downloaded www.stockervale.com, May 29, 2008, 2 pages.

(Continued)

*Primary Examiner* — Edelmira Bosques
(74) *Attorney, Agent, or Firm* — Squire Patton Boggs (US) LLP

(57) ABSTRACT

A delivery catheter for delivery, then photo-activation of photo sensitive material has a photo-sensitive substance-delivery part and an activation part. The catheter delivers substances such as biomaterials to a target site, followed by illumination of the target using optics located at the distal tip of the catheter which are optically coupled to an extracorporeal light source. The light may be delivered by a single or multi-lumen needle, or a separate light guide passed over the catheter.

4 Claims, 7 Drawing Sheets

(56) References Cited

U.S. PATENT DOCUMENTS

| | | |
|---|---|---|
| 7,252,677 B2 | 8/2007 | Burwell et al. |
| 7,344,528 B1 | 3/2008 | Tu et al. |
| 2002/0183738 A1 | 12/2002 | Chee et al. |
| 2002/0192289 A1* | 12/2002 | Zheng et al. ............... 424/486 |
| 2003/0167033 A1* | 9/2003 | Chen et al. ................. 604/20 |
| 2004/0158136 A1* | 8/2004 | Gough .............. A61B 5/14546 600/328 |
| 2004/0230156 A1 | 11/2004 | Schreck et al. |
| 2005/0031281 A1* | 2/2005 | Nath ........................... 385/125 |
| 2005/0070844 A1* | 3/2005 | Chow et al. ............ 604/95.04 |
| 2005/0104059 A1* | 5/2005 | Friedman et al. ............ 257/40 |
| 2005/0107706 A1 | 5/2005 | Zuluaga et al. |
| 2005/0228260 A1 | 10/2005 | Burwell et al. |
| 2006/0211918 A1 | 9/2006 | Lieponis |
| 2007/0083187 A1* | 4/2007 | Eversull et al. .............. 604/508 |
| 2007/0090272 A1 | 4/2007 | Wang |
| 2008/0009751 A1* | 1/2008 | Berndt ................ A61B 5/0075 600/478 |
| 2008/0025943 A1 | 1/2008 | Michal et al. |
| 2008/0027517 A1 | 1/2008 | Burwell et al. |
| 2008/0033339 A1 | 2/2008 | Tulip et al. |

OTHER PUBLICATIONS

StockerYale Inc., Laser Line Generators, LEDs, Specialty fibers, downloaded www.stockeryale.com, May 29, 2008, 1 page.

StockerYale Inc., "Custom-Engineered LED Solutions", downloaded www.stockeryale.com, May 29, 2008, 2 pages.

\* cited by examiner

REDUCED PROFILE AND ENHANCED FLEXIBILITY DELIVERY CATHETERS FOR LIGHT ACTIVATED AGENTS

BACKGROUND OF THE INVENTION

1. Field of the Invention

This invention relates to methods and devices for treating tissue using photo-sensitive substances, such as biomaterials, using a catheter.

2. Description of the State of the Art

Ischemic heart disease typically results from an imbalance between the myocardial blood flow and the metabolic demand of the myocardium. Progressive atherosclerosis with increasing occlusion of coronary arteries leads to a reduction in coronary blood flow, which creates ischemic heart tissue. "Atherosclerosis" is a type of arteriosclerosis in which cells including smooth muscle cells and macrophages, fatty substances, cholesterol, cellular waste product, calcium and fibrin build up in the inner lining of a body vessel. "Arteriosclerosis" refers to the thickening and hardening of arteries. Blood flow can be further decreased by additional events such as changes in circulation that lead to hypoperfusion, vasospasm or thrombosis.

Myocardial infarction (MI) is one form of heart disease that can result from the sudden lack of supply of oxygen and other nutrients. The lack of blood supply may be caused by a closure of the coronary artery (or any other artery feeding the heart) which nourishes a particular part of the heart muscle. The cause of this event is generally attributed to arteriosclerosis in coronary vessels.

Infarct myocardial tissue may be treated by implanting cells, such as mesenchymal stem cells, skeletal myoblasts, bone marrow mononuclear cells, etc., which will facilitate the revitalization of the infarcted heart tissue. Hereafter, these types of materials, as well as solutions containing them, will be referred to as therapeutic agents, agents, biomaterials or photo-activated substances. Delivery of therapeutic agents into the infarct tissue in a minimally-invasive way generally requires that a catheter access the internal heart chamber wall in which the infarcted area exists.

Bioscaffoldings formed of two components and applied in situ to the left heart ventricle can be used to treat post-myocardial infarction tissue damage. "Bioscaffolding", "two-component gelation system" and "gelation system" are terms that are used interchangeably in this context, and are described more fully in U.S. Pub. No. 2008/0025943. Examples of two-component gelation systems include, but are not limited to, alginate construct systems, fibrin glues and fibrin glue-like systems, self-assembled peptides, synthetic polymer systems and combinations thereof. Each component of this two-component gelation system may be co-injected to an infarct region by a dual-lumen delivery device. Examples of dual-lumen delivery devices include, but are not limited to, dual-needle left-ventricle injection devices, dual-needle transvascular wall injection devices and the like.

Another type of therapy exists to introduce chemical compound drugs, sometimes called photosensitizers, into tissue and then excites the photosensitizer in order to enable an energy transfer from the photosensitizer to a nearby oxygen molecule. This produces an excited singlet state oxygen molecule that reacts with nearby biomolecules. This reaction can cause localized damage in target atherosclerotic tissue, for example. The therapy can also be applied in oncology, and may be used to kill cancer cells after they have absorbed a pre-delivered photosensitizer. This therapy thereby provides beneficial effect to the patient.

SUMMARY OF THE INVENTION

According to one aspect of the invention, devices are provided which may be used to deliver biomaterials for cellular cardiomyoplasty. The biomaterials intended for delivery using these devices include photo-polymerizable gels and cells such as autologous or allogeneic adult stem cells, or embryonic stem cells. This includes various embodiments of hydrogel biomaterials for increased efficacy of cellular cardiomyoplasty, improved cell retention at the delivery site, increased cell survival, improved myocardium mechanical properties, and to serve as depots for cytokines. Other materials may be delivered in combination with the photo-polymerizable gels in accordance with these embodiments, as will be appreciated. The disclosure provides devices that are capable of injecting the biomaterials to a target location within the myocardium, and subsequently delivering energy from an optical source to activate the biomaterials. The device also includes features to minimize thermal damage caused by light energy.

The invention provides devices and methods for photo-activated biomaterials, as well as agents that are intended to induce cell necrosis, e.g., as when treating a tumor. According to one aspect of disclosure the material is not photo-activated until after it has been deposited within a tissue. As such, the risks of inducing thrombosis are reduced Words containing the term "photo", such as photosensitive or photo-activated are intended to refer to any band of light that is known, either in the art or as disclosed herein, to have beneficial effects for treatment of conditions using substances that polymerize when exposed to light energy. Accordingly, it will be appreciated that the term "photo" should not be understood as implying that only a particular band of light applies, e.g., visible light, unless the specific context indicates otherwise. As will be apparent from the disclosure, the invention applies to light bands such as NIR, IR, visible and UV light. In a preferred embodiment, IR light is used since its longer wavelength allows it to penetrate deeper into tissue. In this way light capable of activating photo-sensitive substances may be transmitted deeper into tissue while reducing risks of thermal damage to tissue closer to the surface.

According to another aspect of the invention, there is a method and device for injecting and then photo-activating photo polymerizable gels. According to some of these embodiments, a catheter may deliver the gel and light, but separates the two so that the gel is not activated until it is implanted or deposited in the target tissue.

According to another aspect of the invention an improvement over a dual-lumen catheter for treating infarcted heart tissue is provided. In some embodiments a delivery catheter includes a lumen configured to deliver a single photosensitizer, e.g., a photocrosslinkable one component hydrogel (as opposed to a two-component gel). The photo-activated biomaterial is isolated from the light energy until it has been implanted into the tissue. As compared to a dual-lumen catheter which has previously been used to perform a similar treatment, but required a rapid and reproducible mixing of the two or more substances at the tip of the catheter, the method according to the invention may perform the steps where only one lumen is required, a single substance is injected and then a light source is used to activate the substance. In a preferred embodiment the light source and delivery needle may be integrated so that injection and activation of the photosensitive material may be performed at essentially the same time and according to a single invasive procedure.

This invention includes one or more of the following benefits. A premature activation of the photosensitive material is mitigated compared to when multi-component gels are used. A simplicity of design permits single injection and immediate activation "with the flip of a switch". Risks of thrombotic events may be significantly reduced compared to multi-lumen and multi-component gel techniques. Desired flexibility and/ or deliverability properties are not significantly affected when a needle catheter is modified or designed to also include a light emitter for activating photo-activated substances. A light sources can be delivered adjacent or within tissue to better ensure that photo-activated substances are activated after being embedded within a target tissue.

According to another aspect of the invention, a treatment using photosensitive substances may include depositing, then activating the photo-sensitive material using a single catheter. The single catheter may be a single lumen catheter. The single lumen may be a bisected lumen. The light source may be extracorporeal.

According to another aspect of the invention a needle catheter has a light guide configured in a spiral or helical pattern to provide enhanced flexibility for the catheter. The light guide may be encased in a member, e.g., a sheath, that can be passed over the catheter after its distal end has reached target tissue.

According to another aspect of the disclosure a catheter utilizes a needle that both delivers photo-sensitive material to a target tissue and light energy to activate said material in order to provide enhanced flexibility and a reduced profile.

The methods and devices disclosed herein may be used in connection with procedures intended to induce cell growth, e.g., treating infarct tissue, or cell death, e.g., treating a tumor. Accordingly, it will be appreciated that the invention includes methods and devices used in connection with either of these types of procedures.

According to another embodiment, a catheter that injects and light activates may prevent washout (meaning an event where injected material exits from the puncture hole when the needle is removed, as opposed to staying with the tissue as intended). When a material was injected, the needle was removed and then light used to activate material, e.g., using a separate device. The material may exit when the needle is removed. If a photo-polymerizable gel is used in connection with one or more embodiments of the invention, activation using light energy while the needle is embedded will prevent material from exiting through the puncture caused by the needle because gelation occurs while the needle is embedded within the tissue. Thus a method of treating tissue and a catheter having a light emitting end and needle addresses the need for reducing instances of washout as in, for example, when treating heart tissue which is moving continuously as the heart beats. Such a method and apparatus also reduces chances of other complications since the amount of time spent within the heart may be reduced by a catheter that both injects and photo-activates an injected substance.

Embodiments of the invention include one or more of the following additional benefits and advantages.

According to another embodiment, a catheter includes a needle configured for delivery of a photo-active substance to a target tissue, the needle including a piercing tip and a bore; and the needle further comprising a light guide. The needle may include a fiber optic disposed within the bore, in which case the bore may serve to orient the fiber optic. In these embodiments the light is delivered to the target tissue using the pathway provided by the bore, which shapes the fiber optic so that light is guided to the target tissue. In other embodiments a needle forms at least a portion of a light guide, e.g., in the case of a liquid light guide the walls of the bore comprise complimentary refractive or reflective properties of light that together with the transmission properties of the fluid can deliver light from an extracorporeal location to the target tissue.

According to another embodiment, a method for treating tissue, e.g., ischemic heart tissue, includes the steps of placing a catheter distal end adjacent the tissue, the catheter including a needle tip and a light-emitting portion; embedding the tip into the tissue; dispensing a photo-sensitive substance into the tissue; displacing the light emitting portion to enable direct light to reach the tissue, and photo-activating the substance in the tissue.

According to another embodiment, a method for treating tissue includes the steps of disposing a catheter tip adjacent the tissue, injecting a photo-sensitive substance into the tissue using a tip of a needle, and transmitting light energy to the tissue using the needle tip.

According to another embodiment a method for preventing washout of a biomaterial includes the steps of embedding a tip of a needle into the tissue, injecting a photo-polymerizable matrix material (within which a therapeutic biomaterial is suspended) into the tissue using the needle, curing the material using light energy emitted by the catheter, and then withdrawing the catheter from the heart tissue. The light energy may be emitted from the needle tip or a light guide that circumscribes the needle.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION OF THE INVENTION

According to the disclosure, a catheter may include both a needle and a light guide for directing light to a target tissue using an extracorporeal light source. This aspect of the disclosure describes embodiments in which the light is emitted from a light member that is separately configurable with a needle catheter, or integrated into a needle catheter. In an illustrated embodiment a tubular-like structure having embedded fiber-optics is described. The disclosure also describes embodiments in which a lumen for delivery of a photo sensitizer to a target tissue may also serve as a light guide, e.g., by passing one or more fiber-optic strands through the same passage that the photo sensitizer passes, or by using a light-transmitting fluid to direct light to tissue after a photo-sensitizer has been implanted. These later embodiments may be preferred as this may yield a reduced profile catheter having greater flexibility.

Figure 1:
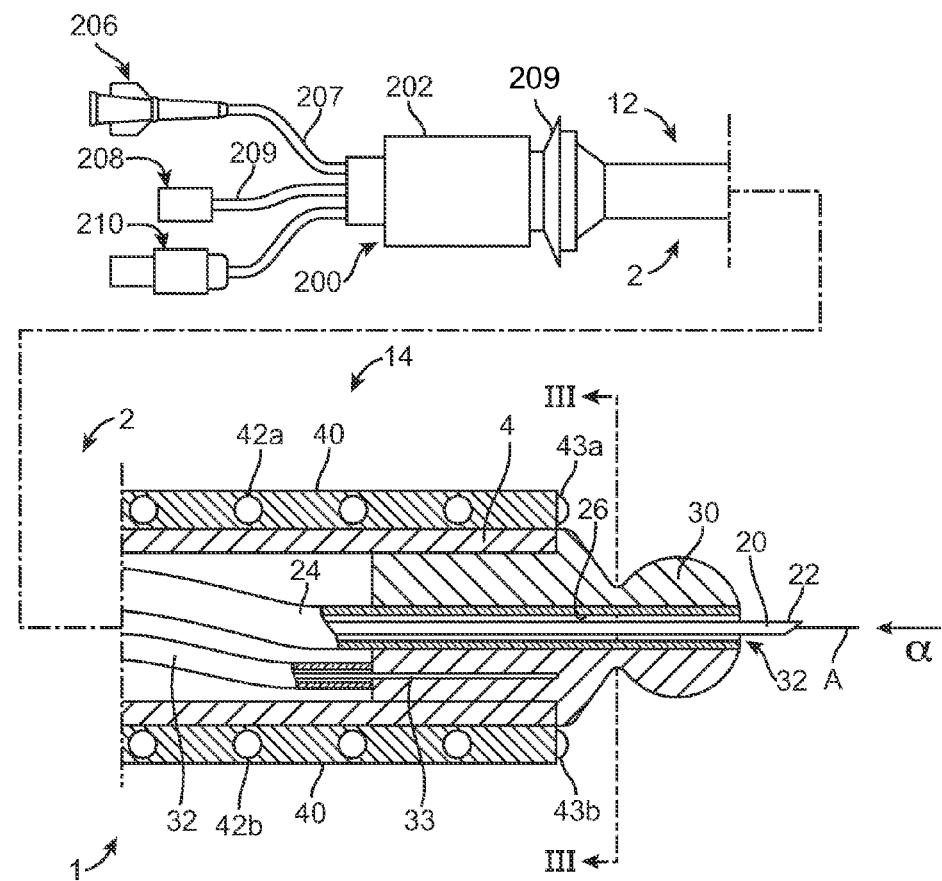
FIG. 1 is side view, partial cross-section of a needle catheter.

FIG. 1 illustrates a partial side view of a needle catheter 1, which has a distal section 14 shown in partial cross-section and a proximal section 12. A shaft or body 2 extends from a controller 200 to a tip 30 of the catheter 1. A jacket 4 extends over the distal portion 14 of the catheter 1 and is flexible in bending yet stiff in axial compression. This jacket 4 is secured to a tip 30. The jacket 4 may also be constructed as a composite piece that includes an inner cage. The catheter may have one or more tendons 33 (movable within tubular members 31) which are used to steer or deflect the catheter 1 as it is passed through an anatomy. The catheter 1 may be steered using a steering portion 209 and handle 202 provided at the proximal end 12 of a controller 200. The controller 200 also includes functional units 206, 208 and 210. In a preferred embodiment these functional units correspond to an optical coupler 208 for transmitting light to a fiber optic bundle (as discussed in greater detail, below), a diagnostic device 210 and a port 206 that receives an injection needle 20. A spherical shape may be used for the tip 30 in order to improve the acoustic properties of the tip 30 when the catheter 1 is imaged by ultrasound, i.e., so that the tip 30 can be easily tracked as it is passed through anatomy. The spherical shape may also improve maneuverability through tortuous anatomy. Further examples are provided in U.S. Pub. No. 2007/0167822. While shape 30 is preferred other tip designs may also be used.

A tubular member 24 extends from the proximal end 12 to the distal end 14. A bore 26, formed by tubular member 24, is sized to provide passage for the injection needle 20, which in FIG. 1 is shown protruding out from an opening 32. Lumen 26 extends from opening 32 at the tip 30 to proximal section 12 where it is in communication with tubular member 207, which connects to port 206. Injection needle 20 may be carried with catheter 1 as it is delivered to a target site, or inserted and then passed over the length of the catheter 1 after the catheter 1 has reached a target tissue.

In some embodiments, a needle is used for delivery of a substance that will be injected into tissue. In other embodiments the needle may serve two roles: injecting the substance into tissue and then photo-activating the substance, as described in greater detail, below. The former embodiments, i.e., no light-transmitting role, is described first in connection with FIGS. 1-6.

Figure 5:
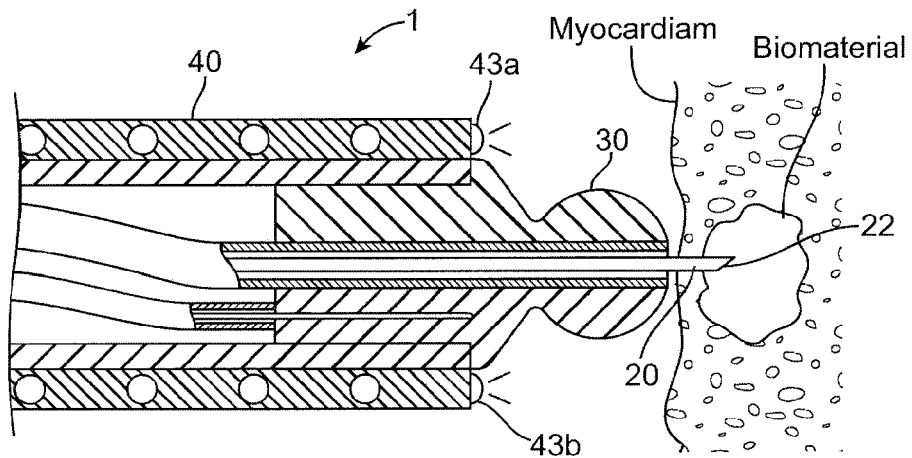
FIG. 5 depicts a method for treating tissue using a delivery catheter according to one embodiment. In this example, an agent, e.g., a photo-polymerizable gel, is inserted into a myocardium wall and then light energy is applied to the tissue to activate the gels. The light source may be an extracorporeal light source according to these methods.

The needle 20 is hollow and may include a beveled tip 22 so that it can easily pierce tissue. An opening 20a located at or near the tip 22 provides access to the lumen formed by the hollow needle 20 body. As depicted in FIGS. 5-6, photosensitive biomaterial is dispensed from the opening 20a after the needle 20 has become embedded in tissue, in this case a wall of the myocardium. The needle 20 is opaque so that photo-sensitive material in the needle 20 does not become exposed to light. Port 206 may be replaced by a port that allows an inserted needle to rotate, and a secondary needle passed in and out of an opening in the injection needle for purposes of providing a wider region of coverage for photosensitive injected biomaterials into a target tissue (without having to remove then reinsert the needle at a new location in order to ensure adequate coverage for all diseased tissue). Examples of this type of injection needle type may be found in U.S. application Ser. No. 12/022,047 filed Jan. 29, 2008. One type of needle port or adapter may be replaced by another using the same catheter and in some cases, during the same procedure. The needle 20 may be extended and retracted through an opening 32 located at the tip 30 by a push and pull motion applied at the proximal end, e.g. a needle portion located at port 206. In other embodiments, the needle 20 may be selectively displaced by a worm gear or other suitable control mechanism (connected as a functional unit to the controller) if more precise extension-retraction control is desirable to ensure the needle 20 is placed at the correct depth within a tissue (see FIG. 5). The distal section 14 may also include anchoring mechanisms that may be useful to prevent the tip 30 from becoming dislodged from the wall of the myocardium during a procedure. Examples of these devices are described in U.S. application Ser. No. 12/022,047 filed Jan. 29, 2008.

Needle catheter 1 includes a unit that is capable of transmitting light from the proximal section 12, i.e., a light source coupled to optical coupler 208, to the distal section 14. According to these embodiments the catheter 1 may therefore be used to both implant or inject photosensitive material as well as administer light therapy to activate the material. As compared to a method in which material is injected locally (or administered intravenously) and then a separate light source is administered according to a different procedure, a method of therapy is offered in which both tasks are accomplished at essentially the same time. A single invasive procedure may accomplish what has required multiple invasive procedures in the past. Thus, for example, in the case where a beating heart is being treated, a method according to the disclosure includes the steps of injecting material directly into the target tissue and then activating said material by the same device that injected the substance. The method offers advantages including a single, simplified procedure as opposed to multiple procedures, reduced risks of thrombosis and greater control over the area that is intended for treatment.

Referring to FIGS. 1-4, a light member 40 is disposed over jacket 4. Member 40 is tubular and includes a plurality of light guides 42 which extend over the length of member 40 and terminate at an optical coupling for a light source connected at the proximal section 12 of the catheter 1. Member 40 may be integral with jacket 4 or separately affixed to the outer surface of jacket 4. In the latter case, member 40 may be part of a functional unit that may be connected to an existing catheter when needed, and removed when not needed. The member 40 may be used to transmit laser light or lamp light, i.e., multiple bands or a narrow band of light. As noted earlier, fiber optic light guides 42 may be used to transmit light. Owing to their flexibility in bending and small size fiber optics are preferred. The light sources, and bands of light include, but are not limited to, a xenon lamp, semiconductor lighting (LED array) or a pulsed laser light, and light bands near infra-red (NIR), IR, visible or UV light. Optical couplers suited for transmitting lamp light or laser light over a narrow or wide bandwidth are known in the art and may be readily modified for use with a needle catheter in view of this disclosure.

Figures 2, 3:
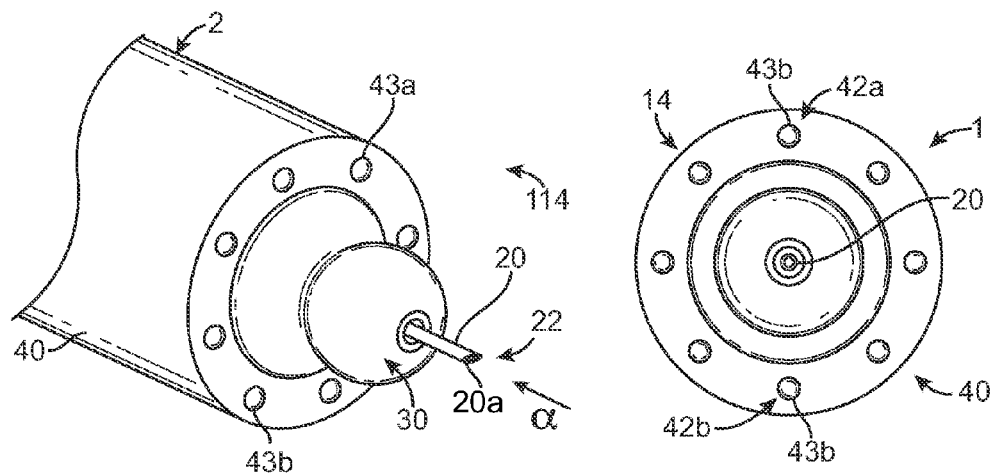
FIG. 2 is a partial perspective view of a distal end of the needle catheter of FIG. 1.
FIG. 3 is a front view of the needle catheter taken at section in FIG. 1.

Referring to FIGS. 1, 2, 3 and 4 the light guides are provided by fiber optics 42. The terminal ends of these fibers, e.g., end 43a and 43b, are arranged to emit light forward of the catheter 1. Preferably, fiber optics 42 are arranged circumferentially about the needle 20, as best depicted in FIG. 3. This allows catheter 1 to provide light everywhere surrounding an injection site for the needle and reduces if not eliminates shadows from forming on the target tissue. As shown in FIG. 3 there are eight optical fibers arranged evenly about the needle 20. There can be more or less optical fibers used. Factors that can influence the selection of, and/or placement of the optical fibers include the coverage area over the tissue, e.g., wide/narrow focus, dispersed light, desired energy flux, the available space at the distal end 14 and the degree to which the optical fibers 42 may effect the stiffness characteristics of the catheter 1.

Figure 4A:
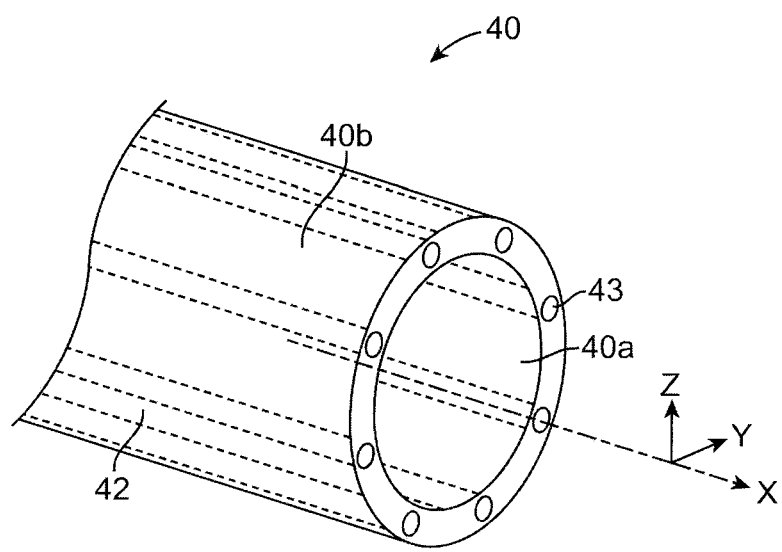
FIGS. 4A-4B are perspective views of two embodiments of an optical bundle contained within a light member. The light member may be separable from a catheter, e.g., connected as a functional unit and removed when not needed for a procedure or passed over the catheter shaft once the catheter distal end has reached the target tissue, integrated within a catheter unitary or composite shaft design, or retrofitted to an existing catheter.
Figure 4B:
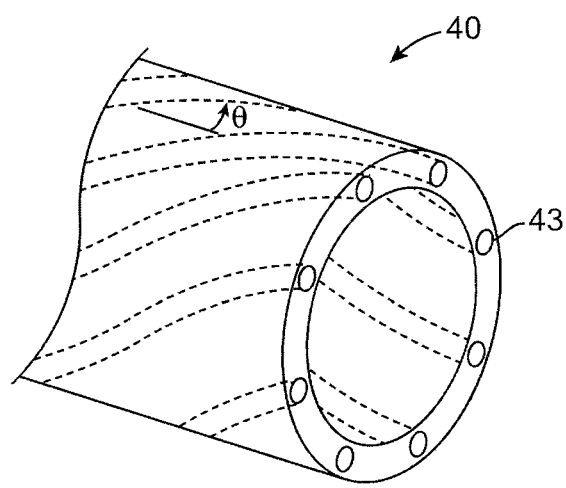

Referring now to FIGS. 4A-4B, there are depicted two embodiments of light member 40. An outer sleeve or sheath 40b and inner sleeve or sheath 40a are suitably chosen to reduce light transmission losses over the length of the catheter shaft 2. According to the two illustrated embodiments, member 40 includes eight separate optical fibers 42, which terminate at a light-emitting end 43 at the distal tip of member 40. The ends 43 are arranged so that light is primarily directed in the X-axis direction.

The arrangement of the optical fibers 42 over the length of the catheter 1 may be varied to achieve a particular degree of flexibility, or maintain such flexibility in the catheter that receives the member 40 over its outer shaft. In the illustrated embodiment, FIG. 1, catheter 1 may have a same or different flexural rigidity about the Y-axis and Z-axis (FIG. 4A). Thus, catheter 1 may require a high degree of flexibility in bending about any axis transverse to the X-axis so that the catheter can easily navigate through tortuous anatomy. Several evenly spaced optical fibers 42 extending longitudinally over the length of the member 40, as depicted in FIG. 4A, may increase the bending stiffness of the catheter 1 that receives member 40. This can be undesirable as it can make it difficult to navigate the catheter 1 with member 40 through tortuous anatomy. For the embodiment depicted in FIG. 4A, the internal forces induced by a bending moment will be carried over a length of the member 40 by the relatively stiff (in axial tension and compression, that is) optical fibers 42. Thus, it may be desirable to arrange the optical fibers 42 so as to minimize any increase in the bending stiffness when the member 40 is integrated with the catheter 1. For example, the optical fibers 42 may be arranged in a helical or spiral pattern having a helix angle θ, as depicted in FIG. 4B. When a spiral arrangement is used, a lesser percentage of the total strain energy is present in the fiber optic material for the same tip 30 deflection. Hence, with a spiral configuration optical fibers 42 may be used without causing an unacceptable increase in the catheter's bending stiffness. The fiber optics may be arranged in varying spiral patterns (i.e., is not constant among each strand) or other non-longitudinal arrangements (FIG. 4A depicts a longitudinal arrangement of fibers) to minimize effects to the bending stiffness of the catheter 1 over one or more longitudinal sections of the catheter. In a preferred embodiment the member 40 is slidable over the catheter (as opposed to being integral with the shaft). These embodiments include the advantage of making the combined body, i.e., shaft 2 and member 40, less stiff in bending than an integrated shaft and member 40.

In the illustrated embodiments the fiber optics ends 43 are arranged so that substantially all of the transmitted light exits these light guides as direct light primarily along the X-axis. This is preferred, although not necessary, for a catheter 1 where biomaterials are injected using a needle and then this material is activated by a light source while the needle remains embedded within the tissue (see FIG. 5). In some embodiments, the dispersion of photosensitive biomaterials in the tissue may be more extensive, in which case a wider distribution of light is desirable. Or the target tissue may be confined to a small area, in which case focused light may be desired, e.g., to reduce power requirements on an extracorporeal light source or to account for transmission losses.

In a preferred embodiment a light member is brought into a near-abutting contact with a surface of the target tissue in order to ensure that all photo-sensitive material receives the adequate amount of light energy to activate. As such, in some embodiments the light member 40 may be configured to be moved forward so that its light-emitting ends 43 are adjacent to tissue, or moved rearward so that more tissue is exposed to direct light. In some embodiments the controller 200 may include a dial and nearby monitor. The dial may be calibrated to movement of the member 40 relative to the distal tip 30 such that a displacement of the ends 43 relative to the opening 32 (see FIG. 1) may be controlled to achieve the desired amount of light distribution over the tissue. Alternatively, or in addition, a correlation may be made between the distance of displacement of the member 40 relative to the tip 30 and the approximate energy flux on the tissue receiving direct light. Thus, a guide may be incorporated at the controller 200 (and/or incorporated into a functional unit for member 40 which includes a monitor) that correlates the operator's displacement of the member 40 over the catheter shaft 2 to the tissue surface area receiving direct light.

Member 40 may be formed from materials that are commonly used to form catheter shafts, e.g., nylon, urethane, polyurethane, polyvinylchloride, polyester, PEEK, PTFE, PVDF, Kyner, polymide, or polyethylene of various suitable densities. Further, the fiber optic strands or cables may be sized to fit within a wall thickness of about 0.005-0.010 inches without any appreciable transmission losses. Thus, a reduced profile catheter may be maintained while providing a light guide capable of transmitting light sufficient to provide the energy flux needed to photo-activate the substance injected into the tissue. In some embodiments the member 40 may be delivered to the site with the catheter. In other embodiments the member 40 may be delivered over the catheter shaft after the photo-activated substances have been injected and the needle remains embedded in the tissue during light treatment.

Other optical elements/techniques may be used to achieve similar purposes. For example, the ends of the elements may be formed as convex or concave lens types, an index of refraction may be chosen to affect the manner in which light is collected/distributed, the ends 43 may be optically connected to a forward diffusion lens, etc. Refracted or reflected light, or a combination thereof may be collected to achieve a particular light distribution over the target tissue. According to these embodiments, the optics associated with member 40 are intended to increase or reduce the area of tissue receiving direct light, which may be desirable from the perspective of photo-activating a larger amount of tissue, increasing the energy flux without increasing power requirements or to make up for transmission losses.

FIG. 5 depicts a cross-sectional side view of the distal end of catheter 1 with the needle 20 penetrated into the myocardium wall and after biomaterials have been injected into the tissue via the needle opening 20*a*. In a method for depositing and then activating biomaterial, e.g., photo-polymerizable gels and cells such as autologous or allogeneic adult stem cells, or embryonic stem cells, the first step is to deliver the catheter tip 30 to the target tissue, in this case the myocardium wall. According to this embodiment the catheter 1 and member 40 are integrated and delivered together. The catheter 1 tip 30 is tracked through the anatomy using ultrasound or other suitable imaging techniques. Once properly positioned adjacent to the myocardium wall, the needle 20 may be inserted into port 206 and then passed up to the opening 32, or the needle 20 may be transported at the same time as the catheter 1, as discussed earlier. Next, the needle 20 is penetrated into the tissue at the desired depth. There may be a high degree of motion of the target tissue during this time. The catheter may in these types of therapies include a deployable anchor that can assist with holding the tip 30 at the desired location during the procedure. The catheter may also incorporate sensors or other means for determining when the tip 30 is placed at the desired location.

After the needle tip 22 has been located in the tissue, the biomaterial is delivered through the needle lumen and deposited within the tissue. The extracorporeal light source, e.g., pulsed laser, xenon lamp, LED array, is then energized and light transmitted over fiber optics 42. This light activates the biomaterial. In one example, IR light is used to penetrate deep into the tissue to activate biomaterial. In some embodiments the light energy may be activated and tissue illuminated at the same time that the biomaterial is being injected into the tissue. This may be desirable over a two-step process as it can reduce the amount of time needed at the target tissue. In alternative embodiments, light with a wavelength in the visible and ultraviolet electromagnetic spectrum may be used for biomaterial activation. It will also be appreciated that a number of light sources exist beyond those previously mentioned for delivering different light wavelengths. For example, numerous electroluminescent, gas discharge, and high-intensity discharge lamps exist that are capable of producing the desired wavelength of light. The light wavelengths and light sources can be identified and chosen based on the specific biomaterial and application that is used.

Figure 6A:
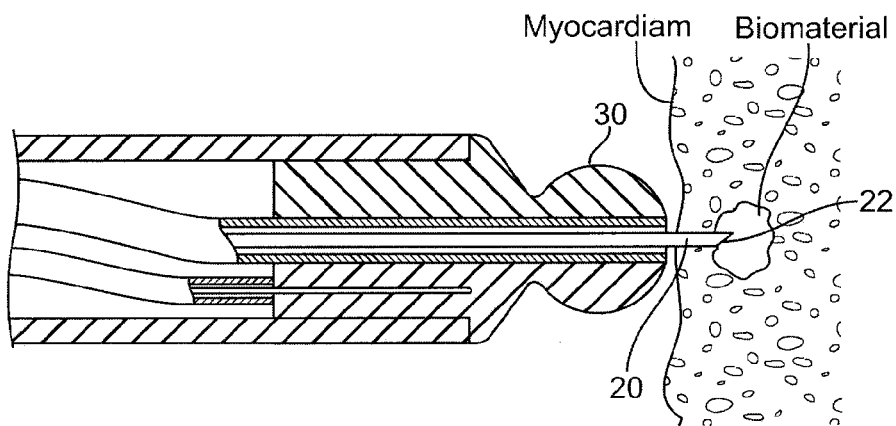
FIGS. 6A-6B depicts a method for treating tissue using a delivery catheter according to another embodiment. As illustrated, a light guide is delivered to a treatment site after the delivery catheter has reached the site. The substance is photo-activated while the needle remains embedded within the myocardial wall.
Figure 6B:
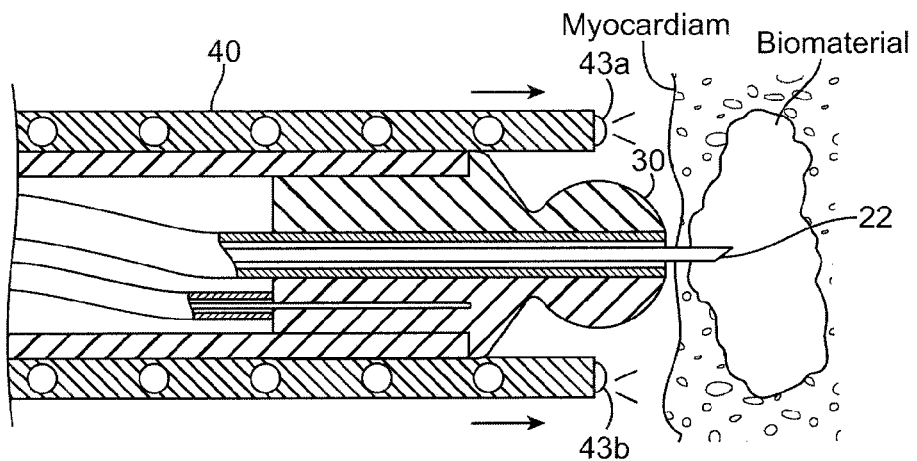

Referring to FIGS. 6A-6B, in an alternative embodiment member 40 may be slidable over the catheter shaft 2 such that it may be positioned closer or further from the myocardium wall, or delivered to the treatment site after the catheter has injected the substance into the tissue (as depicted in the drawings). Thus, in some embodiments a catheter is provided in which the coverage area for light may be focused over a narrow area, or over a broad area, depending on need (as discussed above). For example, if a photo-sensitive material is dispersed over a wide area, the member 40 may be retracted or moved away from the tissue surface so that direct light is received over more tissue surface but where the accompanying lower intensity of light energy is adequate to activate the substance in the tissue. In another example, a biomaterial may be injected deep within the tissue where it is localized to a particular area. In this case, a higher intensity light directed over a smaller area may be preferred. In this case, the member 40 is brought closer to the tissue wall as depicted in FIG. 6B. In other embodiments, the member 40 is delivered to the target tissue and placed at a fixed location relative to the catheter tip 30.

According to the embodiments depicted in FIGS. 6A-6B, the catheter is positioned at the tissue, the needle 20 penetrates the tissue, and biomaterial is injected (as before). Then, the member 40 is delivered over the catheter so that the ends 43 of the optical fibers are located adjacent the tissue. In this embodiment, a method for therapy includes sliding the member 40 over the shaft 2 in two steps, e.g., inject material then photo-activate material. These steps may also occur at essentially the same time. In either case the steps may include positioning the catheter 1 at the tissue, inserting the needle 20 into the tissue, and then sliding the member 40 over the catheter so that the ends 43 are properly positioned relative to the tissue to provide the desired depth, energy flux per unit area, or surface-area coverage of direct light energy for photo-activation. The steps may further include an operator pushing and/or pulling, respectively, a proximal end component coupled to the member 40, so as to achieve a desired position of the ends 43 relative to the tissue, energy flux, coverage area for direct light, and/or simply to place the member 40 at the treatment site (as shown in the drawings). In other embodiments, photo-activation includes the step of pushing the member 40 towards the tissue, i.e., closer to the tip 30 of the catheter 1, and then pulling the member 40 back to its original position when the procedure has concluded. When a wider distribution of direct light is needed, then the member may be pulled away from the tissue, i.e., away from the tip 30, and then pushed back to its starting position (or removed from the catheter 1) when the procedure has completed.

According to another aspect of the disclosure a needle catheter is configured for delivering a photo-sensitive substance to tissue and activating the photo-sensitive substance after it has been injected into tissue using the same passageways for both light activation and injection of a photo-active substance. One advantage of these embodiments is the catheter may be constructed with a reduced profile. These designs may also provide more favorable flexural rigidity properties, and allow greater options for a catheter design since less space is needed to accommodate a light guide. For instance, in view of the disclosure it will be appreciated that a catheter that both delivers a substance and photo-activates a substance may now be used to (1) directly treat tissue in areas that previously might not have been possible due to limited space in the body cavity or passages leading thereto; (2) directly treat tissue in areas that previously would have required a more invasive procedure or multiple procedures; or (3) directly treat tissue with a greater success rate, in the sense that previously it was believed that not all of the substance could be reliably or consistently photo-activated or delivered to where it was intended due to inherent limitations of the medical device(s). The embodiments may also allow more effective photo-activation of substances, especially substances embedded deep within the tissue, since the light emission is delivered using the same passageway(s) that were used to deliver the photo-sensitive substance. These embodiments (as well as those discussed previously) may also minimize occurrences of washout when the needle is removed from the tissue. Examples follow.

Figure 7:
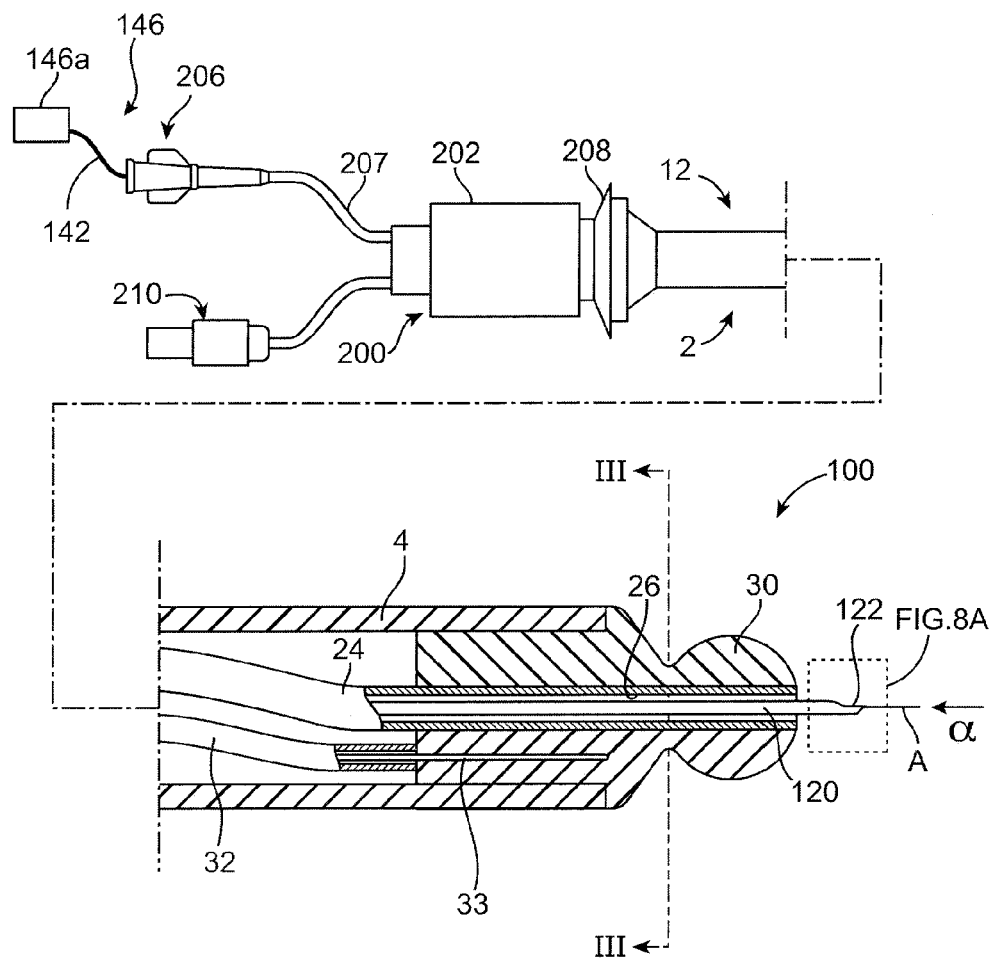
FIG. 7 is side view, partial cross-section of a needle catheter according to other aspects of the disclosure.

Referring to FIGS. 1 and 7, according to some embodiments a needle catheter 100 is configured for injecting tissue, e.g., heart tissue, with a photo-sensitive substance, such as photo-polymerizable gel, and photo-activating the substance after it has been injected into tissue. Catheter 100 may be constructed in a similar manner as catheter 1 depicted in FIG. 1, with the following modifications.

Figure 8A:
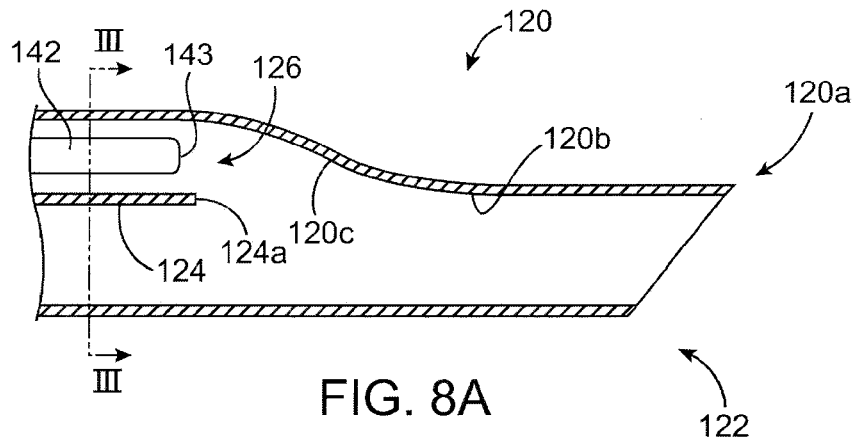
FIGS. 8A and 8B depict a side cross-sectional view of a distal end of a needle of the needle catheter of FIG. 7. According to these embodiments, a needle includes a lumen that is bifurcated so as to form two or more lumens over at least a portion of the needle's longitudinal extent. One lumen may be configured to deliver a photo-sensitive substance to target tissue. A second lumen may house fiber optics. A third, shared common lumen is shared by the fiber optics and the substance.
Figure 8B:
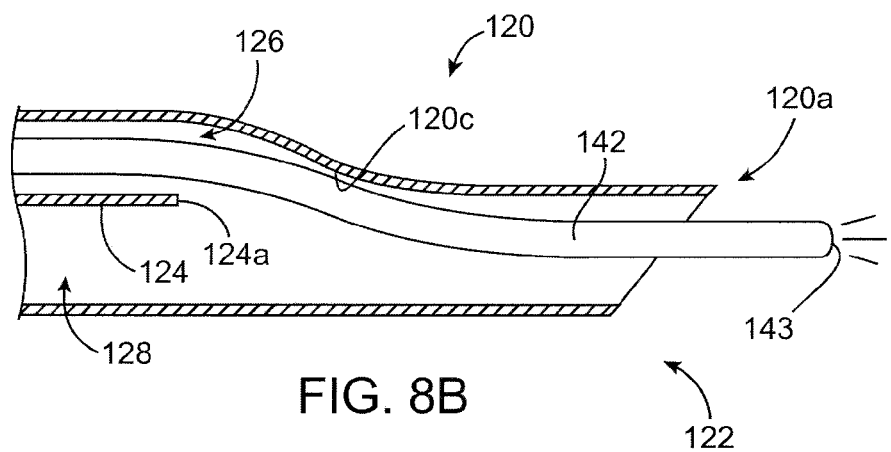
Figure 8C:
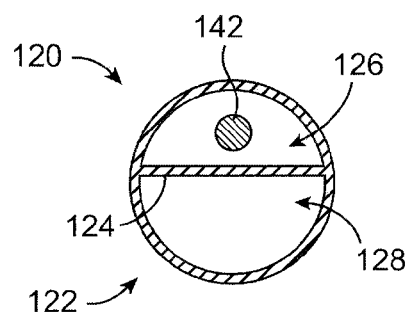
FIG. 8C depicts a front-cross sectional view of the needle distal end of FIGS. 8A-8B taken at section III-III in FIG. 8A.

The light member 40 for catheter 1, integral with or passed over jacket 4 may be removed or not used when operating catheter 100 because catheter 100 is capable of transmitting light for photo-activation by way of a needle lumen. Referring to FIGS. 7 and 8A-8C, a needle 120 having a distal portion 122 is shown extended from the catheter tip opening 32 in FIG. 7. A close-up, cross sectional view of the distal section of the needle 120 is depicted in FIGS. 8A-8C. Needle 120 includes a distal opening 120*a* that may be formed by a tapered, sloped or partially sloped distal portion. The opening 120*a* may be at or near the end of the needle 120. The lumen of the needle 120 is defined by a bore 120*b* which includes a sloped surface 120*c*. An upper lumen 126 and lower lumen 128 is defined within the needle lumen, which lumens 126 and 128 are separated by a separation portion 124. At the proximal end access to the needle lumen may be provided by a port functional unit 206 which may be integrated with the controller 200 or connectable thereto.

A fiber optic 142 (or fiber optic bundle 142) is disposed within the upper lumen 126 that is defined by portion 124 and walls 120*c* and 120*b*. Fiber optic 142 may be displaceable along the length of the needle 120 by the operator pulling or pushing the fiber optic bundle, e.g., using a proximal end gripping member 142 that houses the fiber optics; or by using a mechanism 146*a* incorporated into the fiber optic functional unit 146 for displacing the fiber optics 142 relative to the bore 120*b* (e.g., a plunger, lever, worm gear). The distal end 124*a* of separation portion 124 may be located at or near the distal end 122 of the needle 120 or closer to the needle 120 proximal end. The entrance aperture or opening for the fiber optics may be at the port 206 as illustrated or elsewhere. For instance, an opening for passage of fiber optics 142 may be provided through an opening provided on the controller body 202 that is co-registered with an aperture provided on the needle 20 (not shown). In this way, the procedure associated with injecting the substance and flushing the lumen is not unnecessarily complicated because fiber optics control uses the same entrance to the needle lumen as the substance or flushing fluid. In other embodiments, the port functional unit 206 may integrate fiber optics and/or a fiber optics controller.

Figure 9A:
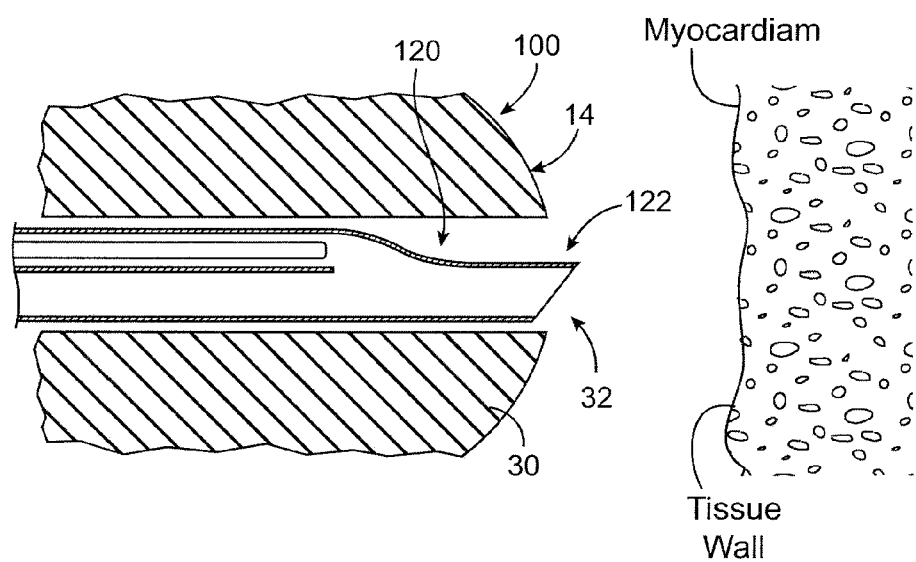
FIGS. 9A-9D depicts devices and methods for treating tissue according to still other aspects of the disclosure. According to these embodiments a single lumen of a needle catheter is used for both delivery of a photo-sensitive material and light energy for photo-activated the substance after it has been injected into a target tissue.
Figure 9B:
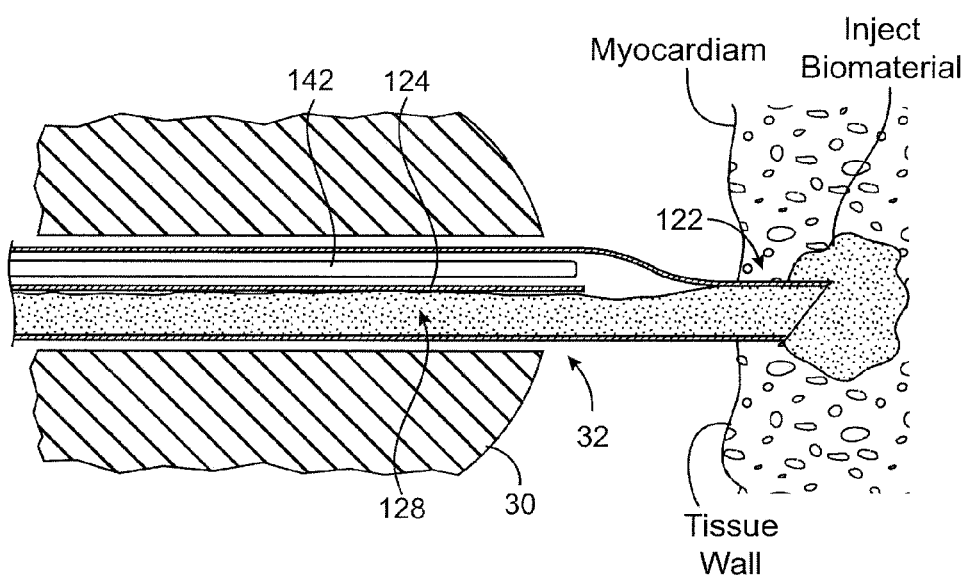

FIG. 8A depicts a position of the fiber optics end 143 adjacent the end 124*a* when the needle 120 is being delivered to the treatment site, and/or when a substance is being injected into the tissue (see, e.g., FIG. 9B). The lower lumen 128 may transport the substance from the proximal end to the distal end 122 while the fiber optics end 143 is positioned near the end 124*a*. As the fiber optics 142 (which may be one or more fiber optic strands or fibers) is advanced, the end 43 may pass over end 124*a* and abut surface 120*c*, thus steering end 143 towards the tapered, common lumen area of the needle lumen. In other embodiments the lumen 126 where the fiber optics 142 resides may instead be used to transport the substance, in which case the fiber optics 142 would not be deflected towards the opening 120*a* but instead could be pushed forward along an essentially straight path towards the opening 120*a*. In any case, the needle 120 may have a common or shared passage proximal to the opening 120*a*, e.g., as illustrated in FIGS. 8A-8B. FIG. 8C illustrates in cross-section (Section in FIG. 8A) the lumens 126, 128 of the needle 120 where the substance and fiber optics 142 may separately reside.

Referring now to FIGS. 9A-9D, according to some embodiments there is a method of treating ischemic heart tissue by injecting and then photo-activating a photo-polymerizable matrix material within which a therapeutic biomaterial is suspended. An advantage of using a gel matrix or other viscous substance in this context is that there is less of a risk that the agent leaves the tissue after the needle tip is withdrawn from the tissue (since the target is moving during the procedure). In other embodiments there are methods for treating tissue using other catheter-delivered agents (including non-viscous suspensions or solutions). In these embodiments, the concerns associated with "washout" may not be relevant given the anatomy being treated. However, the advantages of the methods disclosed herein as applied to these other therapies will be appreciated. Thus, the disclosure is not limited to the case of treating ischemic heart tissue using a photo-polymerizable matrix material within which a therapeutic biomaterial is suspended.

The catheter 100 tip 30 is first placed adjacent a tissue wall, e.g., a wall of the myocardium, as depicted in FIG. 9A. The catheter 100 distal end 14 may be anchored to the tissue wall (as discussed earlier in connection with FIG. 6). Next, the needle 120 is advanced forward and penetrates the myocardial wall. During this time, the fiber optics 142 may reside at the location depicted in FIG. 9B or otherwise be located adjacent the distal end 122 of the needle 120. After the needle 120 is embedded within the tissue the substance, e.g., a biomaterial, may be passed through the lumen 128 and exit the opening 120*a*, as depicted in FIG. 9B. By providing separate lumens 126, 128 the fiber optics may reside within the needle lumen without obstructing the flow of substance to the target tissue. In other embodiments, a needle may be constructed such that a single lumen extends throughout the distal and proximal portions of the needle. In these embodiments the fiber optics may be inserted after the needle has advanced to the target tissue, the substance passed through the needle lumen and deposited into the target tissue, and the needle lumen flushed of the substance. In other embodiments fiber optics may be done away and in its place a liquid light guide may be used to transmit light to the needle tip, as described in greater detail below.

Figure 9C:
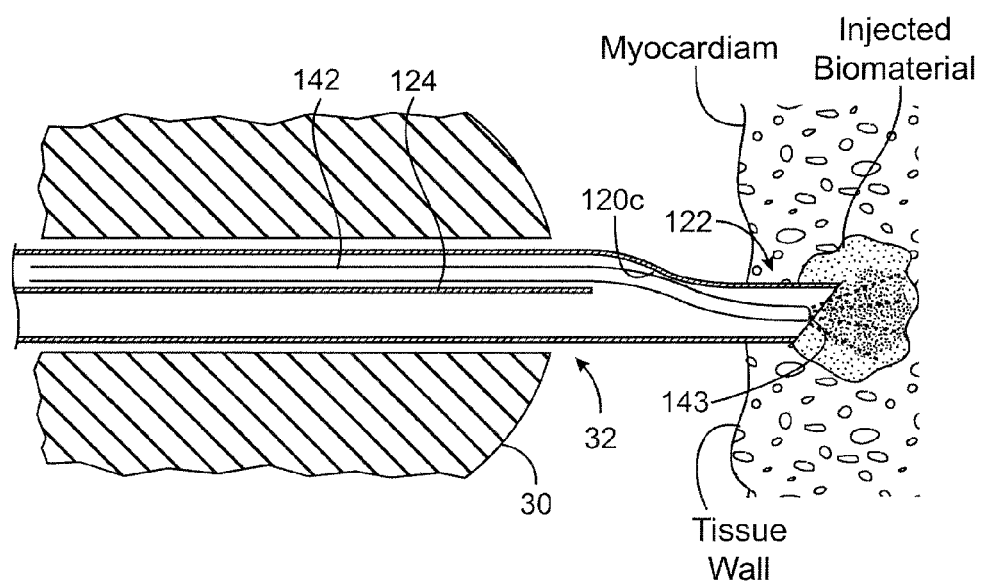

After the substance is injected into the tissue, the needle may be aspirated, i.e., by a flushing fluid, to remove the remaining substance from the lumen, after which the fiber optics 142 may be advanced, e.g., by a pushing force at the proximal end, towards the opening 120*a* such that the fiber optics end 143 is disposed at the opening 120*a* (adjacent the tissue), and light is emitted from the end 143, as depicted in FIG. 9C. In an alternative embodiment, there may be no need to aspirate the needle volume after injecting the substance. Advancement of the fiber optics may provide sufficient force to plunge the remaining substance forward into the target tissue. In order to provide for optimal substance removal in this embodiment, the fiber optic is sized and configured to slide closely within the distal needle portion, thus minimizing dead volume between the fiber optic surface and the needle lumen surface.

Figure 9D:
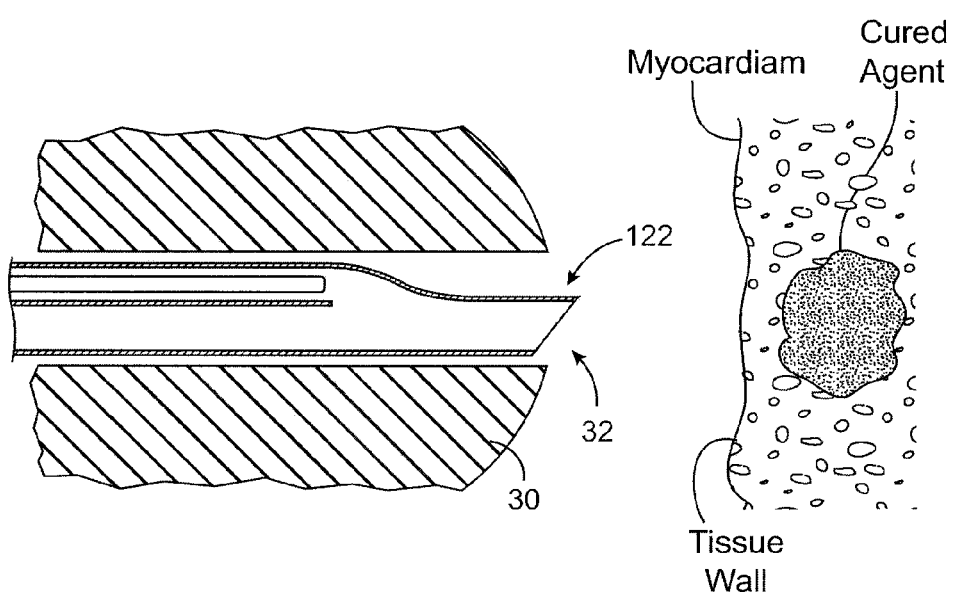

In the case of a photo-polymerizable matrix material that suspends a biomaterial, the light emission step cures this agent suspension. After light treatment, the needle 120 may be removed from the tissue wall as depicted in FIG. 9D. The cured substance, however, does not exit or wash-out (as is sometimes the case for other treatment procedures) when the needle is removed from the tissue. Instead, the curing of the gel matrix can cause the suspended substance to stay with the tissue wall, as opposed to exiting or washing-out from the needle exit-hole in the tissue.

According to another aspect of the disclosure a needle catheter may be used to inject a photo-sensitive substance and photo-activate the substance after it has been implanted into a tissue using a liquid light guide. The needle lumen may be similar to those suited for use in the embodiments described with reference to FIG. 1. That is, the needle 20 may be generally cylindrical in shape with a piercing tip 22 and an exit or opening 20a disposed adjacent the tip. The bore of the needle may have a first refractive index, and the liquid disposed within the lumen may be selected to have a second, complimentary refractive index. The needle bore may be polished to reflect light. Examples of liquid light guide parameters, e.g., material, optics, performance characteristics, light sources, optical couplings, etc. are discussed in U.S. Pat. No. 5,608,834, U.S. Pub. No. 2005/0031281, U.S. Pat. No. 4,009,382, U.S. Pat. No. 5,412,750, and U.S. Pub. No. 2007/0090272. As will be appreciated in light of this disclosure, portions of the disclosures in these references may be suitable for practicing aspects of the invention, or more practical/desirable for a catheter intended to treat certain areas of an anatomy, while other portions of these disclosures may not be suitable, or less practical/desirable.

In some embodiments the light guide may be formed in part by an aspirating fluid for the needle or another light transmitting fluid having favorable light transmission properties. In other embodiments the substance injected into the target tissue may also serve, together with the bore of the needle, as the liquid light guide. The choice of liquid for light transmission will depend on the acceptable level of transmission losses through the liquid, the type of bore surface being used, i.e., the optical properties of the needle material, and the bandwidth of light energy needed to photo-activate the substance, e.g., NIR, IR, visible light or UV. In these embodiments a pulsed laser light, xenon lamp or semiconductor-based light source (LED array) may be used as an extracorporeal source for light transmitted through the liquid light guide.

In a method of photo-activating a substance injected into a target tissue using a needle, the steps may include aspirating the substance remaining in the needle bore using a flushing fluid. After aspiration, a second fluid chosen for its light transmission properties is introduced through the needle lumen. The light is then transmitted through the needle lumen using this liquid light guide. The substance is then activated and remains with the target tissue after gelation has occurred (as discussed earlier), thereby preventing washout from the target tissue when the needle catheter is removed from the tissue. In an alternative embodiment, the substance need not be aspirated from the needle lumen, but instead the second fluid may be delivered behind the substance to drive it into the target tissue. Light may be transmitted through the second fluid once the entire needle lumen has been filled with the second fluid.

As will be appreciated, the invention may be practiced using a variety of catheters. Examples of catheters that may incorporate one or more aspects of the invention include those disclosed in U.S. Publication No. 2005/0070844, U.S. Publication No. 2007/0167822 and U.S. application Ser. No. 12/022,047 filed Jan. 29, 2008.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A catheter having a distal section and a proximal section, the catheter comprising:
   a catheter tip at the distal section of the catheter;
   a needle configured to extend out of and retract into the catheter tip, the needle including a needle tip and a bore, the bore configured to deliver a substance out of the needle tip and to a target tissue;
   a light guide coupled to the catheter tip and configured to emit light from the catheter tip;
   a jacket at the distal section of the catheter; and
   a tubular light member disposed around an outer surface of the jacket,
   wherein the jacket forms an interior passageway, the needle extends through the interior passageway, and the light guide extends through the tubular light member.

2. The catheter of claim 1, wherein the light guide is disposed outside of the bore of the needle.

3. The catheter of claim 1, wherein the tubular light member is slidable on the outer surface of the jacket.

4. The catheter of claim 1, wherein the light guide comprises a plurality of optical fibers, and the optical fibers are arranged circumferentially within the tubular light member.

* * * * *